United States Patent [19]
Davis

[11] Patent Number: 5,784,510
[45] Date of Patent: Jul. 21, 1998

[54] INTENSITY ADJUSTABLE FIBEROPTIC CABLE APPARATUS

[76] Inventor: James M. Davis, 4687 Pond Apple Dr. S., Naples, Fla. 33999

[21] Appl. No.: 719,839

[22] Filed: Sep. 30, 1996

[51] Int. Cl.[6] .................................................. G02B 6/36
[52] U.S. Cl. ........................................ 385/53; 362/32
[58] Field of Search ............................. 362/32; 385/76, 385/901, 31, 32, 77, 137, 53

[56] References Cited

U.S. PATENT DOCUMENTS

| | | | |
|---|---|---|---|
| 5,367,440 | 11/1994 | Gruszczynski et al. | 362/32 |
| 5,400,425 | 3/1995 | Nicholas et al. | 385/76 |
| 5,464,025 | 11/1995 | Charles et al. | 128/849 |
| 5,617,302 | 4/1997 | Kloots | 362/32 |

*Primary Examiner*—Akm E. Ullah
*Attorney, Agent, or Firm*—William E. Noonan

[57] ABSTRACT

An intensity adjustable fiberoptic cable apparatus is disclosed for use in combination with a standard fiberoptic illuminator having a light output port. The apparatus includes an elongate, light transmitting fiberoptic cable. A fitting and an intensity controller, which are attached to a first end of the cable, operably interengage the output port of the fiberoptic illuminator and introduce light generated by the illuminator into the cable. A second fitting and an intensity adjuster, which are attached directly to a distal, second end of the cable, emit transmitted light from the cable.

20 Claims, 3 Drawing Sheets

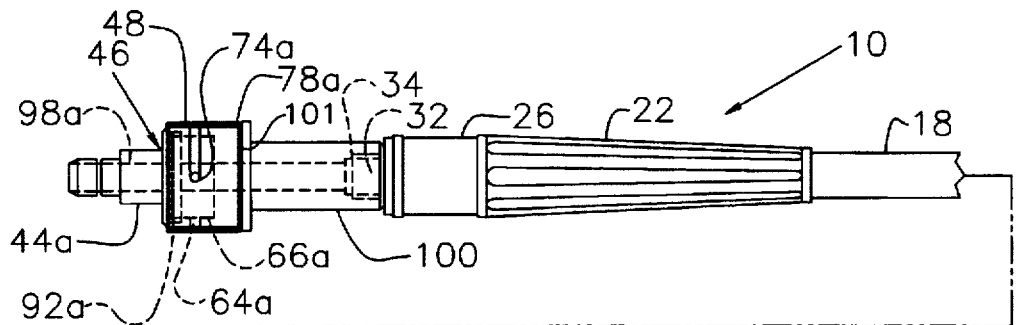
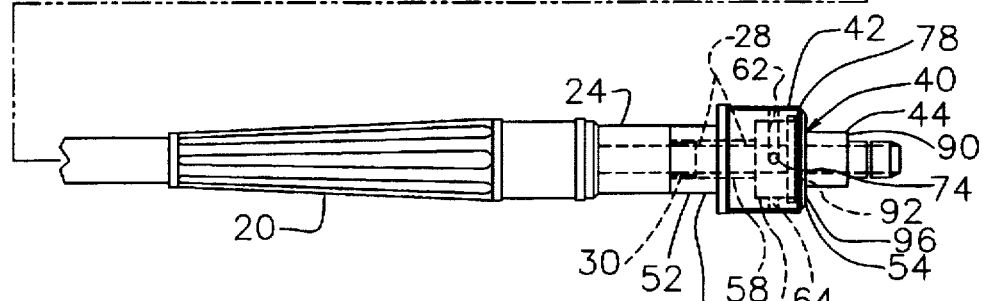
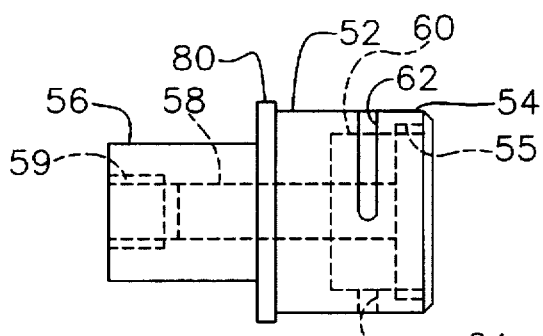
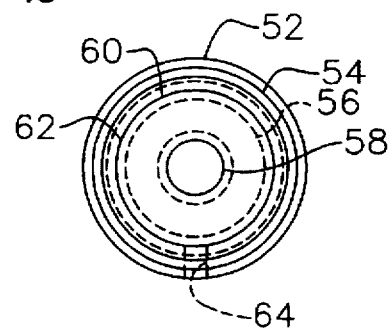
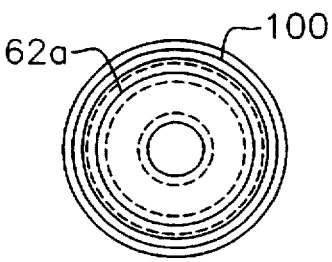
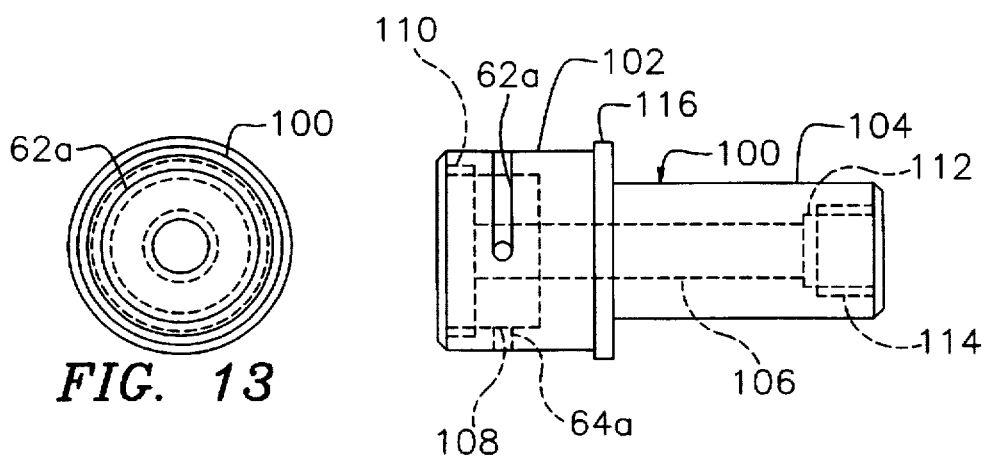

INTENSITY ADJUSTABLE FIBEROPTIC CABLE APPARATUS

FIELD OF THE INVENTION

This invention relates to an intensity adjustable fiberoptic cable apparatus and, more particularly, to a fiberoptic cable apparatus operably interengageable with a standard fiberoptic illuminator and including either one or two adjustment mechanisms that enable the intensity of light being transmitted through the cable to be controlled for use in medical procedures.

BACKGROUND OF THE INVENTION

Fiberoptic illuminators are widely used to provide improved lighting for surgical and other medical procedures. Typically, the light generated by the illuminator is transmitted through a conventional fiberoptic cable to a headlamp, lens or other mechanism, which emits the light in a direction selected by the surgeon or other user of the device. Occasionally, the intensity of this emitted light must be adjusted. For example, the intensity may have to be selected to suit the particular setting or medical procedure that is involved and to provide adequate, but not blinding illumination of the object being illuminated. Traditional illuminators are provided with an integral intensity or brightness knob that controls the light intensity. This knob is usually mounted on the front panel of the illuminator.

Standard intensity adjustment knobs have serious limitations. To personally make the necessary adjustment, the surgeon or other person manipulating the cable must have immediate access to the front panel of the illuminator. Space and distance limitations often render this impractical or impossible. Moreover, adjusting the intensity may divert the attention of the user away from the patient. This is obviously highly undesirable, particularly in surgical settings where the operator's full attention to the patient is mandated. Accordingly, in most applications, a nurse, technician or other assistant is required to adjust the light intensity while the doctor manipulates the cable. This procedure also has its shortcomings. The doctor must communicate the precise lighting requirements to the person operating the intensity adjustment knob. Because two persons are involved, it tends to be quite difficult to precisely obtain the required degree of lighting. Communicating back and forth with the assistant can also divert the doctor's attention from the patient. And, using an assistant to adjust the intensity of the transmitted light obviously necessitates the added expense and involvement of additional personnel. Such personnel are prevented from performing other necessary tasks.

Some simpler, less expensive illuminators lack intensity adjustment controls altogether. Such devices emit a light beam of constant intensity. Accordingly, these instruments have only limited usefulness and are particularly inconvenient for surgical applications.

SUMMARY OF INVENTION

It is therefore an object of the present invention to provide an intensity adjustable fiberoptic cable that permits light intensity adjustments to be made quickly, conveniently, accurately and personally by the surgeon or other person manipulating the cable.

It is a further object of this invention to provide an intensity adjustable fiberoptic cable apparatus that permits the intensity of light from a fiberoptic illuminator to be adjusted without having to directly access the illuminator or manipulate dials or knobs on the illuminator.

It is a further object of this invention to provide a fiberoptic cable apparatus that permits the intensity of light transmitted through the cable to be adjusted virtually instantaneously by the person using the cable without diverting that person's attention from the task at hand and without requiring the user to communicate intensity requirements to an assistant or other personnel.

It is a further object of this invention to provide an intensity adjustable fiberoptic cable apparatus that reduces the number of persons required for certain medical procedures and surgical operations, and which makes more efficient and better use of available medical personnel.

It is a further object of this invention to provide an intensity adjustable fiberoptic cable apparatus that permits lighting intensity to be adjusted much more quickly and accurately than has heretofore been possible.

It is a further object of this invention to provide a fiberoptic cable apparatus having mechanisms located at either end of the cable for adjusting light intensity so that intensity adjustments may be achieved in a much more flexible and versatile manner.

It is a further object of this invention to provide a mechanism that permits the user to adjust the light intensity from a fiberoptic illuminator that is otherwise designed to emit light of a constant intensity.

This invention results from a realization that fiberoptic cable intensity adjustments may be made much more quickly, accurately and efficiently by providing an intensity adjuster or controller at a distal end of the fiberoptic cable. This permits intensity adjustments to be made directly by the surgeon, doctor or other personnel manipulating the cable and pointing it at the object being illuminated. This intensity adjustment supplements the conventional adjustments located directly on the illuminator and significantly facilitates the use of fiberoptic illuminators in surgical and other medical operations. A similar controller at the opposite end of the cable allows a constant intensity illuminator to be retrofit for intensity adjustment.

The invention features an intensity adjustable fiberoptic cable apparatus for use in combination with a standard fiberoptic illuminator having a light output port. The apparatus includes an elongate, light transmitting fiberoptic cable. There are means attached to a first end of the cable for operably interengaging the output port of the fiberoptic illuminator and introducing light generated by the illuminator into the cable for transmission therethrough. Means are located proximate and attached directly to a distal second end of the cable for emitting transmitted light from the cable. The means for emitting include means for selectively adjusting the intensity of the light emitted from the cable.

In a preferred embodiment, the means for adjusting may include an adjuster housing that is connected to the second end of the cable and has means defining an interior passageway through which light from the cable is transmitted. The means for adjusting further include an adjustable iris disposed within the housing and extending across the passageway and means for selectively opening and closing the iris a chosen amount to adjust the intensity of the light passing through the iris. The second end of the cable may carry a threaded portion that interengages a complementary threaded section of the housing. The threaded section of the housing may include a threaded receptacle that interengages the threaded portion of the cable. The housing may include an elongate slot adjacent to the iris. The means for selectively opening and closing the iris may include a handle operably attached to the iris and extending through the slot.

The handle is movable in a first direction to open the iris and in an opposite second direction to close the iris. The iris may have a generally circular shape and the handle may extend radially from the iris. The housing may include a circular, cross sectional shape and the means for selectively opening and closing may include a generally annular component disposed circumferentially about and mounted for selectively rotating on the housing. The annular component may be attached to the handle such that rotation of the annular component about the housing in the first direction moves the handle in the first direction to open the iris and, rotation of the annular component in the second direction moves the handle in the second direction to close the iris. The annular member may include a hole that receives the handle to secure the annular component to the handle. The handle may include an upper end that terminates not higher than the outer circumferential surface of the annular component.

The means for emitting may include a fitting that is attached to the means for adjusting. The fitting may include a channel that conducts light from the means for adjusting and a discharge opening formed at the end of the channel. Light is emitted through the discharge opening from the apparatus. The fitting may comprise a fiberoptic plug that is selectively engageable with a lamp such that the light emitted from the discharge opening of the fitting is projected by the lamp.

The means for operably interengaging may include means for selectively controlling the intensity of light introduced into the cable. The means for selectively controlling may include a controller housing that is connected to the first end of the cable and has means defining an interior conduit through which light from the illuminator is introduced. The means for controlling may further include an adjustable controller iris disposed within the controller housing and extending across the conduit, and means for selectively opening and closing the controller iris a chosen amount to adjust the intensity of the light introduced through the controller iris into the cable. The controller housing may include an elongate slot adjacent to the controller iris. The means for selectively opening and closing the controller iris may include a controller handle operably attached to the controller iris and extending through the slot on the controller housing. The controller handle is movable in a first controller direction to open said controller iris and an opposite second controller direction to close said controller iris. The controller iris may have a generally circular shape and the controller handle may extend radially from the controller iris. The controller housing preferably has a circular cross sectional shape and the means for selectively opening and closing the controller iris may include a controller ring disposed circumferentially about and mounted for rotating on said controller housing in the first and second controller directions. The controller ring is attached to the controller handle such that rotation of the ring about the controller housing in the first controller direction moves the controller handle in the first controller direction to open the controller iris. Rotation of the ring in the opposite second controller direction moves the controller handle in that direction to close the controller iris. The ring includes a hole that receives the controller handle to secure the ring to the controller handle. The controller handle may include an upper end that terminates not higher than the circumferential surface of the ring.

The means for operably interengaging may include a second fiberoptic fitting attached to the means for controlling. The second fitting may include an inlet through which light is introduced into the cable apparatus from the illuminator and a channel that conducts light from the inlet to the means for controlling.

DETAILED DESCRIPTION OF PREFERRED EMBODIMENTS

Other objects, features and advantages will occur from the following description of preferred embodiments and the accompanying drawings, in which:

FIG. 2 is an elevational side view of the cable apparatus;

FIG. 3 is an elevational side view of the intensity controller housing located proximate the end of the cable apparatus that is interengaged with the fiberoptic illuminator;

FIG. 4 is an elevational end view of the housing of FIG. 5;

FIG. 12 is an elevational side view of the adjuster housing located at the distal end of the fiberoptic cable apparatus; and FIG. 13 is an elevational end view of the adjuster housing of FIG. 12.

Figure 1:
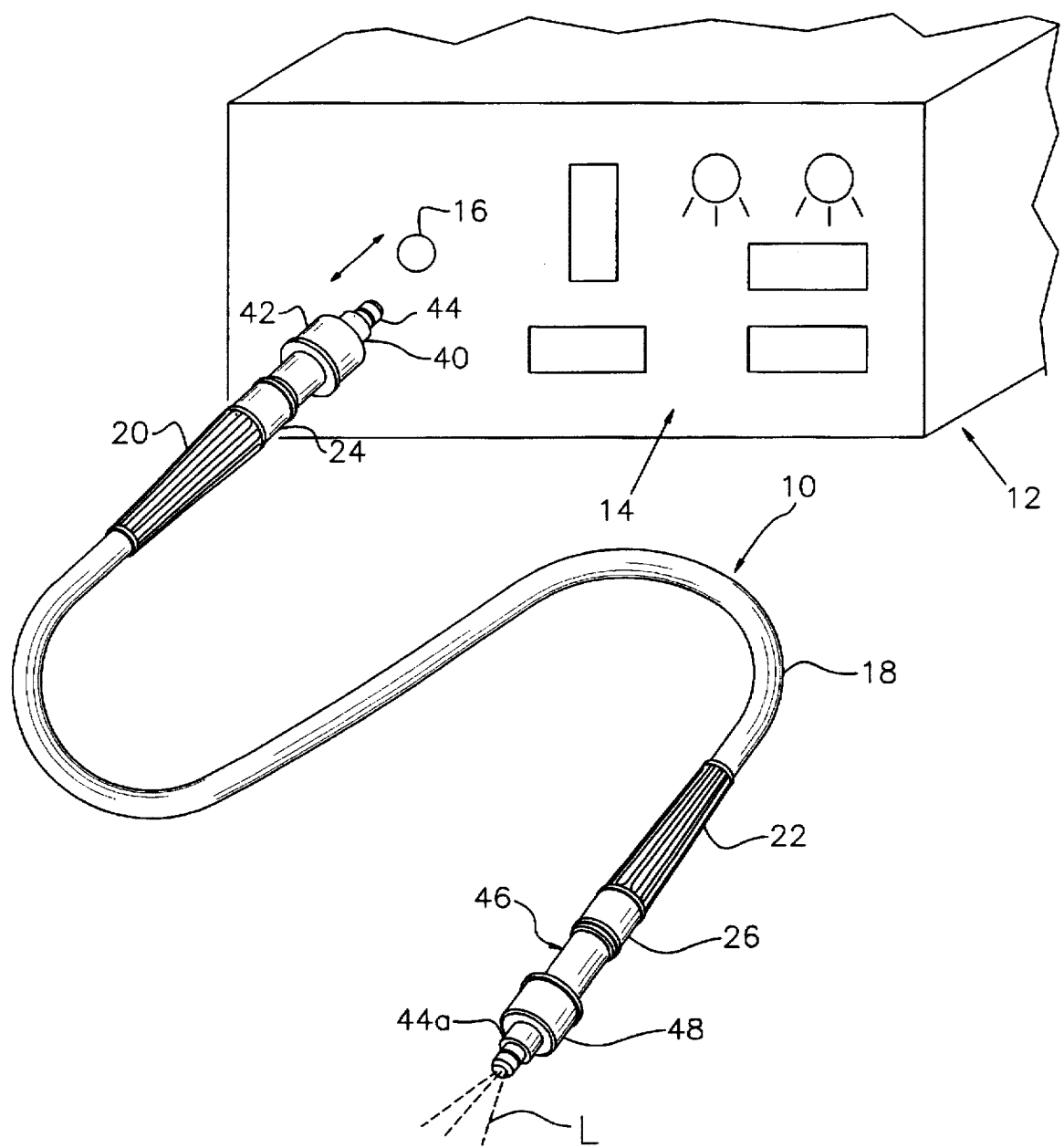
FIG. 1 is a perspective view of an intensity adjustable fiberoptic cable apparatus according to this invention, and a standard fiberoptic illuminator with which the cable apparatus is used.

There is shown in FIG. 1 an intensity adjustable fiberoptic cable apparatus 10, which is selectively interengaged and used with a standard fiberoptic illuminator 12. The cable apparatus may be utilized with a wide variety of conventional fiberoptic illuminators. Such illuminators are widely used by the medical profession to provide lighting for surgery and other types of medical procedures. A typical fiberoptic illuminator 12 includes various dials and gauges 14, as well as an output port 16 that is operably engageable with a plug or fitting at the end of a standard fiberoptic cable. Illuminator 12 produces a desired type of light (e.g. halogen, neon, etc. ) and this light is introduced through port 16 into the fiberoptic cable interengaged with the outlet port. This light is then transmitted through the attached fiberoptic cable and directed to a surgical headlamp, lens or other apparatus, which emits the light toward a selected object to be illuminated. It should be noted that the particular construction and features of the fiberoptic illuminator are not limitations of this invention. All that is required is that the illuminator include one or more light outlet ports. For the purposes of illustration and clarity, FIG. 1 depicts only a single outlet port 16. Cable apparatus 10 may be utilized with illuminators having various other numbers and configurations of output ports. An alternative arrangement of outlet ports are illustrated in the turret mechanism disclosed in U.S. patent application Ser. No. 08/384,927 filed Feb. 7, 1995.

Cable apparatus 10 is designed to operably interengage output port 16 of fiberoptic illuminator 12 in a manner analogous to that of a standard fiberoptic cable. Apparatus 10 includes an elongate fiberoptic cable portion 18 that may have any selected length. Cable portion 18 comprises a conventional, universal fiberoptic cable having a construction that should be well known to those skilled in the art. As further shown in FIG. 2, a tapered casing portion 20 is carried by cable 18 proximate a first end of cable apparatus 10 (the end closest to illuminator 12) and a second tapered casing portion 22 is carried proximate the opposite, distal end of apparatus 10. A stepped bushing 24 is attached to casing portion 20. A cylindrical bushing 26 is similarly attached to casing portion 22. Fiberoptic cable 18 extends generally centrally through casing portions 20 and 22. As best shown in FIG. 2, cable 18 includes an optical fiber 28, which extends beyond the distal end of bushing 24 and carries a plurality of circumferential threads 30. These threads enable fiber 28 to be interengaged with an intensity control mechanism located proximate the right-hand end of cable apparatus 10, in a manner described more fully below. The opposite end 32 of fiber 28 extends from cylindrical bushing 26 at the other end of cable 18. Fiber end 32 carries circumferential threads 34, which permit that end of the cable to interengage the intensity adjustment mechanism located at the left-hand end of apparatus 10 in FIG. 2. Again, this threaded interconnection is described more fully below.

A device 40 attached to one end of fiber 28 (the right-hand end in FIG. 2) selectively interengages output port 16 of illuminator 12 to operably interconnect cable apparatus 10 to the fiberoptic illuminator. More specifically, device 40 includes an intensity controller mechanism 42, which is attached directly to cable 18, and an attached fiberoptic end fitting comprising a plug 44. This plug is inserted into port 16 to operably interengage the cable apparatus with the fiberoptic illuminator.

The opposite end of cable apparatus 10 includes a device 46 for emitting light transmitted through cable 18. Device 46 includes an intensity adjuster mechanism 48, which is secured directly to end 32 of fiber 28. A second fitting, comprising a fiberoptic plug 44a is carried by adjuster 48. As will be described more fully below, plug 44a either emits transmitted light directly from cable 18 or transmits that light to an auxiliary device such as a headlamp or lens from which the light is emitted.

The intensity of the light transmitted through cable apparatus 10 is selectively adjusted by either controller mechanism 42 or adjuster mechanism 48. These mechanisms are constructed and operate in a similar fashion. The specific structure of each of the mechanisms and the manner in which they are interconnected to fiberoptic cable 18 will now be explained.

Controller mechanism 42 includes a controller housing, shown alone in FIGS. 3 and 4. The controller housing has a generally circular cross sectional shape, best shown in FIG. 4, and includes a main body portion 54 and an extension portion 56 that is unitarily interconnected with main body 54 and extends to abut the distal end of cable bushing 24, in the manner shown in FIG. 2. Housing 52 has a generally cylindrical shape and features a central conduit 58 that extends completely through body 54 and extension portion 56. A transverse cavity 60 having a generally circular cross sectional shape is formed within body portion 54. A circumferential slot 62 is formed in body 54 and, as best shown in FIG. 4, extends approximately 90 degrees about the circumference of the body. Slot 62 communicates with interior cavity 62 such that the interior cavity is exposed through the slot. A threaded recess 55 is formed about the interior circumference of cavity 60 proximate the right-hand end of housing 52. See FIG. 3. This threaded recess enables the housing 52 and entire controller mechanism 42 to interengage plug 44 located at the end of apparatus 10. This interconnection is described is described more fully below.

Conduit 58 includes threads 59 located at one end of the conduit (the left-hand end in FIG. 3). These threads are interengaged with the threads 30, FIG. 2, carried by fiber 28. As a result, a standard optical fiber is received by conduit 58 and threadably interconnected with housing 52. One end of fiber 28 is disposed adjacent to housing cavity 60.

Figure 5:
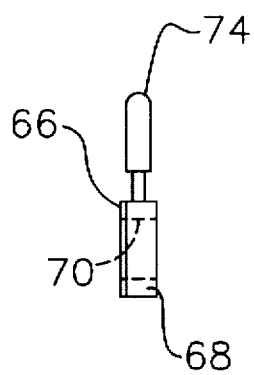
FIG. 5 is an elevational side view of a representative iris used in each of the intensity adjustment mechanisms of this invention.
Figure 6:
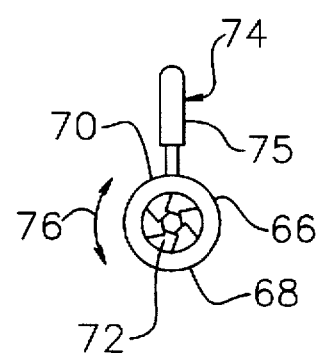
FIG. 6 is an elevational front view of the iris of FIG. 5.

As shown in FIG. 2, an adjustable diameter iris 66, shown alone in FIGS. 5 and 6, is mounted within cavity 60 of controller housing 52 such that it extends transversely across conduit 58. A set screw 64 is formed through the wall of body 54 adjacent cavity 60. The set screw is tightened to secure the iris within cavity 60. As a result, optical fiber 28 is positioned immediately adjacent one side of iris 66 (i.e. the left-hand side in FIGS. 2 and 5).

As best shown in FIGS. 5 and 6, iris 66 comprises a standard adjustable iris apparatus having a circular configuration. The iris apparatus includes an annular frame 68 having a central opening 70. A plurality of plate-like iris elements 72 are formed in an interleaved or fan-like fashion within opening 70. A handle 74 is operably interconnected to iris elements 72 through frame 68. Handle 74 is moved selectively back and forth, as indicated by double-headed arrow 76, through a circumferential slot in frame 68 such that the iris is selectively opened and closed, as desired. Rotating handle 74 in one direction (either clockwise or counter clockwise) widens or opens iris 72 and rotating the handle in the opposite direction narrows or closes the iris. Furthermore, the degree of rotation determines the extent to which the iris is opened or closed.

In FIGS. 5 and 6, iris 66 is shown with a conventional full handle 74, including a relatively wide portion 75. Preferably, when iris 66 is installed within cavity 60, the wide outer end 75 of handle 74 is removed so that the handle does not extend to the height illustrated in FIGS. 5 and 6. Rather, the handle is shortened such that it engages but does not extend beyond an annular component or ring that is rotatably mounted about housing 52. This construction is described more fully below.

Figure 7:
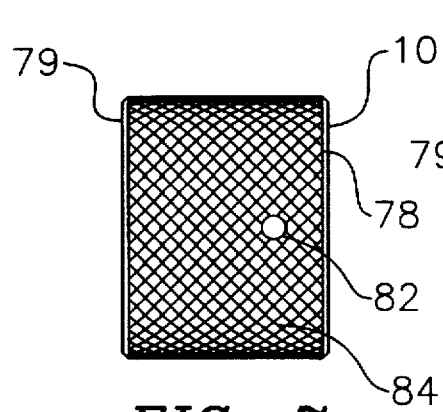
FIG. 7 is an elevational side view of a representative rotatable annular component or ring used on each of the intensity adjustment mechanisms of this invention.
Figure 8:
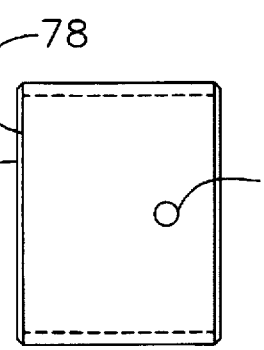
FIG. 8 is a cross sectional view of the annular adjustment component.
Figure 9:
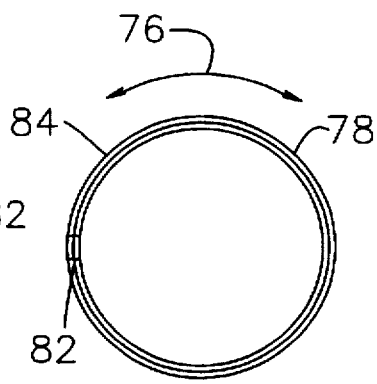
FIG. 9 is an elevational end view of the annular adjustment component.

As shown in FIG. 2, an annular intensity controller ring 78, shown alone in FIGS. 7–9, surrounds and is rotatably mounted on controller housing 52. More particularly, ring 78 is rotatable about body 54, best shown alone in FIG. 3, such that one edge of ring 79, FIGS. 7 and 8, abuts a flange 80, shown in FIG. 3, of housing 52. A hole 82 is formed through the ring for receiving handle 74 of iris apparatus 66. As previously explained, handle 74 is cut off such that it does not extend beyond the outer surface of ring 78. As best shown in FIG. 7, outer surface 84 contains a knurled pattern that facilitates gripping the ring and rotating it about controller housing 52 in the manner indicated by double headed arrow 76 in FIG. 9.

Figure 11:
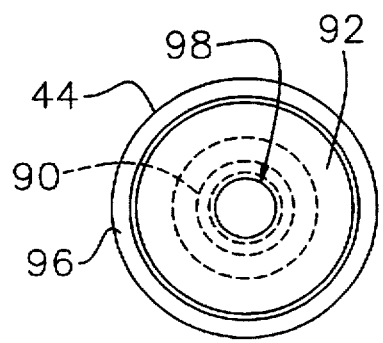
FIG. 11 is an elevational end view of the fitting of FIG. 10.
Figure 10:
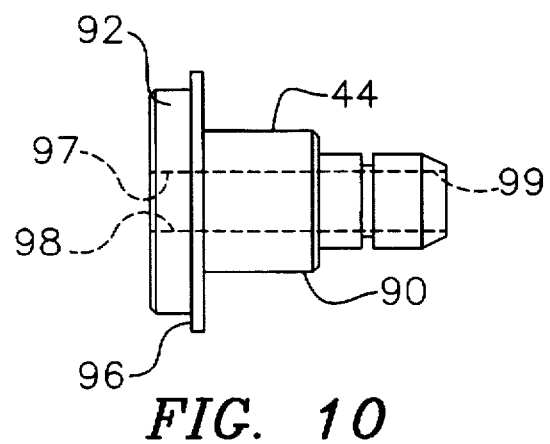
FIG. 10 is an elevational side view of a representative one of the fiberoptic end fittings of the cable apparatus.

FIGS. 10 and 11 depict plug 44. The plug comprises a standard fiberoptic fitting that operably and communicably interengages output port 16 in FIG. 1 to introduce light from the fiberoptic illuminator into the fiberoptic cable. Specifically, plug 44 includes an exterior body portion 90, an interior threaded portion 92 and an annular flange 96 that separates portions 90 and 92. An interior channel 98 extends fully through plug 44 from an inlet 100 to discharge opening 102. Typically, a light conducting rod is formed in channel 98.

Plug 44 is communicably secured to controller mechanism 42 in the manner shown in FIG. 2. Specifically, interior portion 92 of plug 44 is interengaged with threaded recess 55 of controller housing 52. As a result, body 90 of plug 44 extends to the right from housing 52. Threaded annular portion 92 is disposed immediately adjacent one side of iris 66, i.e. the right-hand side in FIG. 2. Plug 44 and fiber 28 are therefore located adjacent opposite sides of iris 66.

Emitter device 46, FIG. 2, features a construction that is analogous to but slightly different from that of interengagement device 40. In particular, the emitter device includes an iris, intensity adjusting ring and end plug that are identical to the components described above. Accordingly, these features of the emitter device are referred to herein by the reference numerals previously used for corresponding elements of the interengagement device, accompanied by lower case "a" designations.

The left-hand, distal end of apparatus 10 comprises a separate and distinct intensity adjuster mechanism 48 and a light emitting end plug 44a. Adjuster 48 employs an adjuster housing 100, shown in FIGS. 12 and 13. Housing 100 includes a generally cylindrical main body portion 102 and a generally cylindrical extension portion 104 that is interconnected unitarily to and extends from main body portion 102. The extension portion has a diameter that is somewhat smaller than the diameter of the main body portion. A central passageway 106 extends fully through the main body portion 102 and extension portion 104. A transverse cavity 108 having a generally circular cross section is formed in main body portion 102 at one end of passageway 106 (the left-hand end in FIG. 12). The entrance of cavity 108 includes threads 110. Similarly, a receptacle 112 is formed at the opposite end of housing 100 and, more particularly, within extension section 104 at the right-hand end of passageway 106. Receptacle 112 also includes threads 114 formed about its interior circumferential surface. An elongate slot 62a extends circumferentially about main body portion 102 for approximately 90 degrees.

Referring to FIGS. 2, 12 and 13, end 32 of optical fiber 28 is attached to the righthand end of adjuster housing 100. More particularly, threads 34 of fiber end 32 operably interengage threads 114 within chamber 112. The fiberoptic cable thereby terminates within chamber 112. The light emitting end of the fiberoptic cable is adjacent to and communicates with passageway 106. As a result, light emitted from end 32 of fiber 28 is transmitted through passageway 106.

An iris 66a, constructed identically to iris 66, FIGS. 2, 5 and 6, is mounted within cavity 108 of housing 100. A set screw 64a is employed to secure iris 66a in place within cavity 108. As with the iris apparatus in the previously described intensity controller mechanism, iris 66a is mounted within cavity 108 such that it extends transversely across light transmitting passageway 106. A handle 74a, FIG. 2, extends from iris 66a and is interconnected to an annular adjuster component or ring 78a. This adjuster component is constructed identically to the intensity adjusting ring 78 of FIGS. 7–9. Component 78a is disposed about and rotates on main body 102 of adjuster housing 100. Edge 101 of component 78a engages flange 116 of housing 100. Annular component 78a includes a hole (see hole 82 in FIGS. 7–9) that receives and selectively operates handle 74a (which, like previously described handle 74, is cut off at the surface of the annular component). Annular component 78a again operates handle 74a of iris 66a when the annular component is rotated in a clockwise or counterclockwise manner, as indicated by doubleheaded arrow 76 in FIG. 9. This widens or narrows iris 66a, as desired, to provide a selected light intensity through the adjuster 48.

End plug 44a is mounted to adjuster 48 in a manner similar to the previously described means for mounting end plug 44 to intensity controller 42. Plug 44a includes each of the elements of plug 44, FIGS. 10 and 11. In particular, plug 44a includes a threaded interior portion 92a that is interengaged with threads 110 of cavity 108, shown in FIG. 12. This secures plug 44a to adjuster 48 so that the plug extends from the adjuster in the manner shown in FIGS. 1 and 2. Again, a central channel 98a is formed through plug 44a and a discharge opening is formed at the distal end of this channel. As a result, light transmitted through adjuster 48 and into plug 44a is emitted from the plug as indicated by light beam L in FIG. 1. In certain embodiments, the plug may be interconnected to a surgical headlamp, lens apparatus or some other structure for projecting or otherwise emitting the light.

The particular materials used to construct the cable, adjustment mechanisms and fittings should be of the type commonly used in fiberoptic, medical and surgical applications. Preferably, stainless steel and other durable, high quality metals, metal alloys and plastics are employed.

In operation, apparatus 10 is assembled in the manner described above. In particular, intensity controller 42 and end plug 44 are interconnected to a first end of cable 18. Intensity adjuster 48 and end plug 44a are operably secured to the opposite end of cable 18. Plug 44 is interengaged with fiberoptic illuminator 12 by inserting that fitting into output port 16. As a result, light is introduced through the channel 98 of plug 44 into the fiberoptic cable apparatus. Intensity may be adjusted at the first end of the cable apparatus through operation of intensity controller 42. Ring 78 is rotated clockwise or counterclockwise, as required, to selectively open (widen) or close (narrow) the iris a chosen amount. As the iris is widened, the intensity of light transmitted through the fiberoptic cable increases. Conversely, as the iris is narrowed, the intensity decreases. Controller 42 permits intensity to be adjusted at the illuminator panel, even when the illuminator lacks its own intensity control knob. As a result, less expensive constant intensity illuminators may be retrofit with an intensity control mechanism. This improves the usefulness of these devices considerably.

Alternatively, intensity may be independently adjusted at the opposite, distal end of the fiberoptic cable apparatus. Annular component 78a of intensity adjuster 48 is rotated, again in either a clockwise or a counterclockwise direction, to selectively open and close iris 66a a chosen amount. This causes light L of a desired intensity to be emitted from plug 44a or from an optical apparatus attached to that plug.

Significant advantages are achieved by locating an intensity controller at the distal end of the cable apparatus. Most significantly, this apparatus permits the fiberoptic cable intensity adjustments to be performed, independently of the illuminator and at the distal end of the cable, by the surgeon or other person handling the fiberoptic cable. This user can adjust the intensity instantaneously and without having to divert his or her attention from the task at hand. Likewise, the intensity adjustments can be made without requiring the assistance of additional personnel to control the intensity at the illuminator. Such personnel are thereby free to perform other needed tasks. The ability for the doctor or other person using the cable to personally perform the intensity adjustments also eliminates extraneous communications between that person and assisting personnel and eliminates the possibility of miscommunications. Intensity adjustments are accomplished far more effectively, quickly and efficiently than has been possible using conventional fiberoptic illuminators.

It should be understood that, although the embodiment shown herein employs an intensity adjustment mechanism at each end of the fiberoptic cable, in alternative embodiments the intensity controller located proximate the illuminator may be eliminated and intensity adjustment capability may be provided only at the distal end of the fiberoptic cable. This is the end that is being handled by the surgeon or other personnel using the fiberoptic cable and, therefore, it is most important that independent intensity adjustment be provided at that end.

Although specific features of the invention are shown in some drawings and not others, this is for convenience only, as each feature may be combined with any or all of the other features in accordance with the invention. Other embodiments will occur to those skilled in the art and are within the following claims.

What is claimed is:

1. Intensity adjustable fiberoptic cable apparatus for use in combination with a standard fiberoptic illuminator having a light output port, said apparatus comprising:

an elongate, light transmitting fiberoptic cable;

means, attached to a first end of said cable for operably interengaging the output port of the fiberoptic illuminator and introducing light generated by the illuminator into said cable for transmission therethrough;

a light emitting component; and intensity adjustment means, which are distinct from said light emitting component and which communicably interconnect said light emitting component and a distal second end of said cable, for transmitting light from said cable to said light emitting component and selectively adjusting the intensity of the light emitted from said light emitting component without being disconnected from said cable.

2. The apparatus of claim 1 in which said intensity adjustment means includes an adjuster housing that is connected to said second end of said cable and has means defining an interior passageway through which light from said cable is transmitted, said intensity adjustment means further including an adjustable iris disposed within said housing and extending across said passageway and means for selectively opening and closing said iris a chosen amount to adjust the intensity of light passing through said iris.

3. The apparatus of claim 2 in which said second end of said cable carries a threaded portion that interengages a complementary threaded section of said housing.

4. The apparatus of claim 2 in which said housing includes an elongate slot adjacent to said iris, said means for selectively opening and closing said iris including a handle operably attached to said iris and extending through said slot, said handle being movable in a first direction to open said iris and an opposite second direction to close said iris.

5. The apparatus of claim 4 in which said iris has a generally circular shape and said handle extends radially from said iris.

6. The apparatus of claim 1 in which said light emitting component includes a fitting, attached to said means for adjusting, said fitting including a channel that conducts light from said means for adjusting and a discharge opening formed at the end of said channel and through which light is emitted from said apparatus.

7. The apparatus of claim 6 in which said fitting comprises a plug that is selectively engageable with a lamp such that light emitted from said discharge opening of said fitting is projected by said lamp.

8. The apparatus of claim 1 in which said means for operably engaging include means for selectively controlling the intensity of the light introduced into said cable.

9. An intensity adjustable fiberoptic cable apparatus for use in combination with a standard fiberoptic illuminator having a light output port, said apparatus comprising:

an elongate, light transmitting fiberoptic cable;

means attached to a first end of said cable for operably interengaging the output port of the fiberoptic illuminator and introducing light generated by the illuminator into said cable for transmission therethrough, said means for operably interengaging including means for selectively controlling the intensity of the light introduced into the cable; said means for controlling including a controller housing that is connected to said second end of said cable and has means defining an interior conduit through which light from said illuminator is introduced to said cable, said means for controlling further including an adjustable controller iris disposed within said controller housing and extending across said conduit and means for selectively opening and closing said controller iris a chosen amount to adjust the intensity of light passing through said controller iris; and means, located proximate and attached directly to a distal second end of said cable, for emitting transmitted light from said cable, said means for emitting including means for selectively adjusting the intensity of the light emitted from said cable; said means for adjusting including an adjuster housing that is connected to said first end of said cable and has means defining an interior passageway through which light from said cable is transmitted, said means for adjusting further including an adjustable iris disposed within said adjuster housing and extending across said passageway and means for selectively opening and closing said iris disposed in said adjuster housing a chosen amount to adjust the intensity of light emitted by said cable.

10. An intensity adjustable fiberoptic cable apparatus for use in combination with a standard fiberoptic illuminator having a light output port, said apparatus comprising:

an elongate, light transmitting fiberoptic cable;

means attached to a first end of said cable for operably interengaging the output port of the fiberoptic illuminator and introducing light generated by the illuminator into said cable for transmission therethrough, said means for operably interengaging including means for selectively controlling the intensity of the light introduced into the cable; and means, located proximate and attached directly to a distal end of said cable, for emitting transmitted light from said cable.

11. Intensity adjustable fiberoptic cable apparatus for use in combination with a standard fiberoptic illuminator having a light output port, said apparatus comprising:

an elongate, light transmitting fiberoptic cable;

means, attached to a first end of said cable for operably interengaging the output port of the fiberoptic illuminator and introducing light generated by the illuminator into said cable for transmission therethrough; and means, located proximate and attached directly to a distal second end of said cable, for emitting transmitted light from said cable, said means for emitting including means for selectively adjusting the intensity of the light emitted from said cable, said means for adjusting including an adjuster housing that is connected to said second end of said cable and has means defining an interior passageway through which light from said cable is transmitted, said means for adjusting further including an adjustable iris disposed within said housing and extending across said passageway and means for selectively opening and closing said iris a chosen amount to adjust the intensity of light passing through said iris, said housing including an elongate slot adjacent to said iris, said means for selectively opening and closing said iris including a handle operably attached to said iris and extending through said slot, said handle being movable in a first direction to open said iris and an opposite second direction to close said iris, said iris having a generally circular shape and said handle extending radially from said iris, said housing having a circular cross sectional shape and said means for selectively opening and closing including a generally annular component disposed circumferentially about and mounted for selectively rotating on said housing in said first and second directions, said annular component being attached to said handle such that rotation of said annular component about said housing in said first direction moves said handle in said first direction to open said iris and rotation of said annular component in said second direction moves said handle in said second direction to close said iris.

12. The apparatus of claim 11 in which said annular component includes a hole that receives said handle to secure said annular component to said handle.

13. The apparatus of claim 2 in which said handle includes an upper end that terminates proximate the circumferential surface of said annular component.

14. Intensity adjustable fiberoptic cable apparatus for use in combination with a standard fiberoptic illuminator having a light output port, said apparatus comprising:

an elongate, light transmitting fiberoptic cable;

means, attached to a first end of said cable for operably interengaging the output port of the fiberoptic illuminator and introducing light generated by the illuminator into said cable for transmission therethrough; and means, located proximate and attached directly to a distal second end of said cable, for emitting transmitted light from said cable, said means for emitting including means for selectively adjusting the intensity of the light emitted from said cable;

said means for operably engaging including means for selectively controlling the intensity of the light introduced into the cable, said means for controlling including a controller housing that is connected to said first end of said cable and has means defining an interior conduit through which light from said illuminator is introduced, said means for controlling further including an adjustable controller iris disposed within said controller housing and extending across said conduit and means for selectively opening and closing said controller iris in a chosen amount to adjust the intensity of light introduced through said iris controller into said cable.

15. The apparatus of claim 14 in which said controller housing includes an elongate slot adjacent to said iris, said means for selectively opening and closing said controller iris including a handle operably attached to said controller iris and extending through said slot in said controller housing, said handle being movable in a first direction to open said controller iris and in an opposite second direction to close said controller iris.

16. The apparatus of claim 15 in which said controller iris has a generally circular shape and said controller iris handle extends radially from said controller iris.

17. The apparatus of claim 16 in which said controller housing has a circular cross sectional shape and said means for selectively opening and closing said controller iris include a ring component disposed circumferentially about and mounted for selectively rotating on said housing in said pair of opposing controller adjustment directions, said ring component being attached to said controller handle such that rotation of said ring component about said housing in said first controller adjustment direction moves said handle in said first controller adjustment direction to open said iris and rotation of said ring component in said second controller adjustment direction moves said handle in said second controller adjustment direction to close said iris.

18. The apparatus of claim 17 in which said ring component includes a hole that receives said controller handle to secure said ring component to said controller handle.

19. The apparatus of claim 18 in which said controller handle includes an upper end that terminates not higher than the circumferential surface of said ring component.

20. The apparatus of claim 14 in which said means for operably interengaging include a second fitting attached to said means for controlling, said second fitting including a controller channel that conducts light through said means for controlling and an inlet opening formed at the end of said controller channel and through which light is introduced from said illuminator.

* * * * *